73-633 SR

5/13/86 XR 4,587,971

United States Patent [19]

Stolfi et al.

[11] Patent Number: 4,587,971

[45] Date of Patent: May 13, 1986

[54] ULTRASONIC SCANNING APPARATUS

[75] Inventors: Fred R. Stolfi, Shrub Oak; Robert L. Maresca, Ossining; Peter P. Adamovic, Irvington, all of N.Y.

[73] Assignee: North American Philips Corporation, New York, N.Y.

[21] Appl. No.: 676,461

[22] Filed: Nov. 29, 1984

[51] Int. Cl.[4] .............................................. A61B 10/00

[52] U.S. Cl. ...................................... 128/660; 73/633; 73/634; 310/36

[58] Field of Search .................. 310/168, 36; 335/272; 128/660, 661; 73/618, 633, 634

[56] References Cited

U.S. PATENT DOCUMENTS

| | | | |
|---|---|---|---|
| 3,949,250 | 4/1976 | Walker et al. | 310/36 |
| 3,956,678 | 5/1976 | Byrne et al. | 310/168 |
| 3,959,672 | 5/1976 | Walker et al. | 310/36 |
| 4,013,911 | 3/1977 | Fujiwara et al. | 310/168 |
| 4,092,867 | 6/1978 | Matzuk | 128/660 |
| 4,164,722 | 8/1979 | Garvey | 310/36 |
| 4,257,272 | 3/1981 | Sloman | 73/633 |
| 4,398,425 | 8/1983 | Matzuk | 73/633 |
| 4,399,703 | 8/1983 | Matzuk | 128/660 |
| 4,433,691 | 2/1984 | Bickman | 128/660 |
| 4,479,388 | 10/1984 | Matzuk | 128/660 |
| 4,515,017 | 5/1985 | McConaghy | 128/660 |

*Primary Examiner*—Kyle L. Howell
*Assistant Examiner*—Ruth S. Smith
*Attorney, Agent, or Firm*—Marc D. Schechter

[57] ABSTRACT

An ultrasonic scanning apparatus includes a rotor, first and second electromagnetic stators, and an ultrasonic transducer mounted on the rotor. Each electromagnetic stator has two curved pole faces arranged opposite pole faces on the rotor. The electromagnetic stators are arranged on opposite sides of the axis of rotation of the rotor. The stator pole faces are tapered such that on rotation of the rotor in one direction, the gaps between the rotor and a first stator decrease while the gaps between the rotor and the other stator increase. On rotation of the rotor in the opposite direction, the gaps between the rotor and the first stator increase and the gaps between the rotor and the second stator decrease. Means are provided for alternately energizing the first and second electromagnetic stators to cause the rotor to oscillate about the axis of rotation.

7 Claims, 5 Drawing Figures

FIG.1
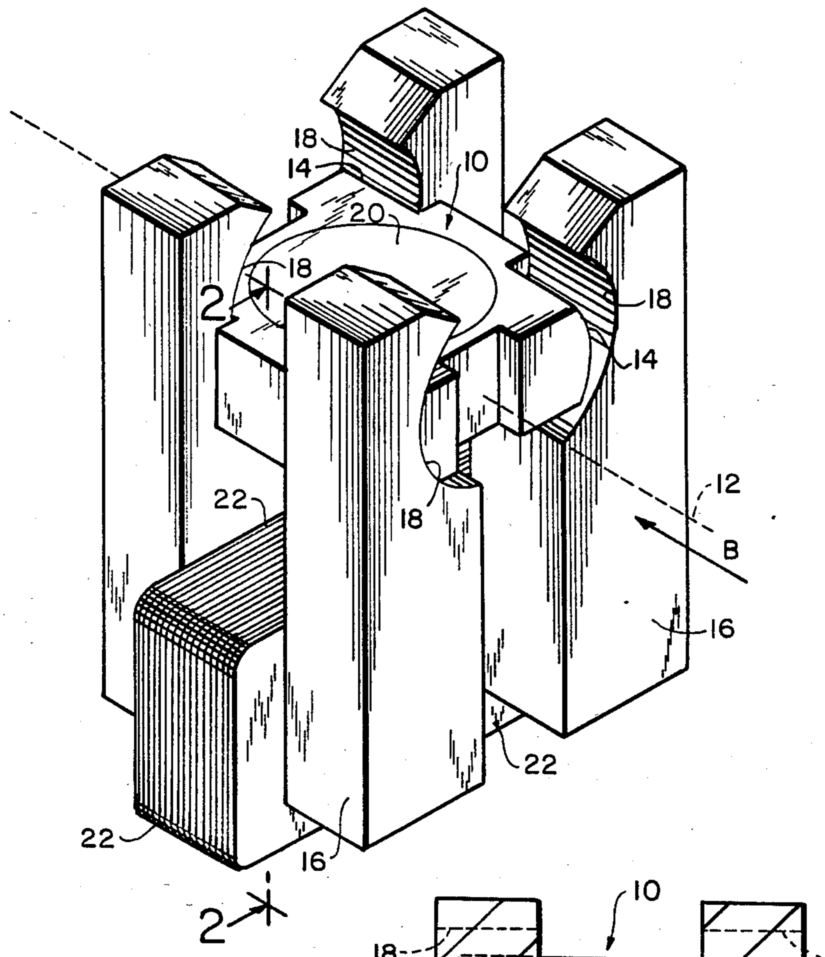
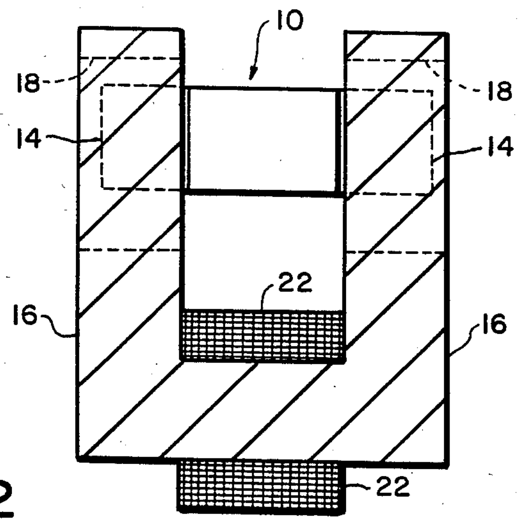
FIG.2

ULTRASONIC SCANNING APPARATUS

BACKGROUND OF THE INVENTION

The invention relates to ultrasound imaging devices, such as for medical applications. More particularly, the invention relates to a device for scanning an ultrasonic transducer across a body, in order to produce an image of a cross-section through the body.

In ultrasonic "A-scanners", an ultrasonic transducer generates an acoustic pressure signal and projects the signal in a straight line through a body. The projected signal is scattered along its path of propagation, and as a result generates an echo acoustic pressure signal. The echo pressure signal contains information regarding the nature of the body along the path of propagation. The ultrasonic transducer receives the echo pressure signal, and converts it into an electrical signal.

A two-dimensional image of a cross-section through the body is obtained in an ultrasonic "A-scanner", by pivoting the ultrasonic transducer through a selected angular range in order to scan the cross-sectional layer. Each electrical echo signal represents an image of a line in the layer; all the electrical echo signals together represent an image of a pie-shaped cross-sectional layer of the body. By suitable processing of the electrical echo signals, an image of the layer can be displayed on, for example, a cathode ray tube screen.

SUMMARY OF THE INVENTION

It is an object of the invention to provide a device for pivoting an ultrasonic transducer over a selected angular range to scan a layer of a body.

It is another object of the invention to provide a device for oscillating an ultrasonic transducer back and forth over a selected angular range to continuously scan a layer of a body.

It is a further object of the invention to provide a device for generating an angular position signal representing the angular position of an oscillating ultrasonic transducer.

It is another object of the invention to use the angular position signal in a closed-loop feedback system for controlling the angular position of the ultrasonic transducer as a function of time.

It is still another object of the invention to feed the angular position signal to display electronics for displaying the signal generated by the ultransonic transducer.

According to the invention, an ultrasonic scanning apparatus includes a rotor, and first and second electromagnetic stators. An ultrasonic transducer is mounted on the rotor. Means are provided for alternately energizing the first and second electromagnetic stators to cause the rotor to oscillate about its axis of rotation.

The rotor is made of a material having a positive magnetic susceptibility. The rotor has first and second pole faces on a first side of the axis of rotation, and has third and fourth pole faces on a second side of the axis of rotation opposite to the first side. All four pole faces are oriented away from the axis of rotation.

The first electromagnetic stator is arranged on the first side of the axis of rotation. The first stator has two curved pole faces arranged opposite the first and second rotor pole faces. The stator pole faces are separated from the rotor pole faces by gaps. The first stator pole faces are tapered such that on rotation of the rotor in a first direction from a first point to a second point, the gaps between the first stator pole faces and the rotor pole faces decrease. The first stator and the rotor form a first magnetic circuit whose major reluctance is in the gaps.

The second electromagnetic stator is arranged on the second side of the axis of rotation, and has two curved pole faces arranged opposite the third and fourth rotor pole faces. The second stator pole faces are separated from the rotor pole faces by gaps. The second stator pole faces are tapered such that on rotation of the rotor in a second direction, opposite the first direction, from the second point to the first point, the gaps between the second stator pole faces and the third and fourth rotor pole faces decrease. The second stator and the rotor form a second magnetic circuit whose major reluctance is in the gaps between the second stator pole faces and the rotor pole faces.

Preferably, the means for energizing the electromagnetic stator comprises means for generating an angular position signal representing the actual angular position of the rotor around the axis of rotation. The energization means further includes means for generating a reference signal representing the desired angular position of the rotor as a function of time. Control means alternately energizes the first and second electromagnetic stators in response to the difference between the angular position signal and the reference signal.

The angular position signal may be generated, according to the invention, by means for measuring the reluctance of at least one magnetic circuit. Since the gap between the pole faces varies as a function of the angular position, the reluctance of the magnetic circuit will also vary as a function of the angular position.

The reluctance of the magnetic circuit can be measured by means for generating a high frequency electric signal and coupling it into an electromagnetic stator, and means for measuring the changes in the high frequency signal due to its coupling to the electromagnetic stator.

Each electromagnetic stator according to the invention includes an element having a positive magnetic susceptibility. An electrically conductive coil is wrapped around this element.

BRIEF DESCRIPTION OF THE DRAWING

FIG. 1 is a perspective view of a first embodiment of an ultrasonic scanning apparatus according to the invention.

FIG. 2 is a partly cross-sectional, partly schematic view of the ultrasonic scanning apparatus of FIG. 1 along the line 2—2.

DESCRIPTION OF THE PREFERRED EMBODIMENTS

Figure 3:
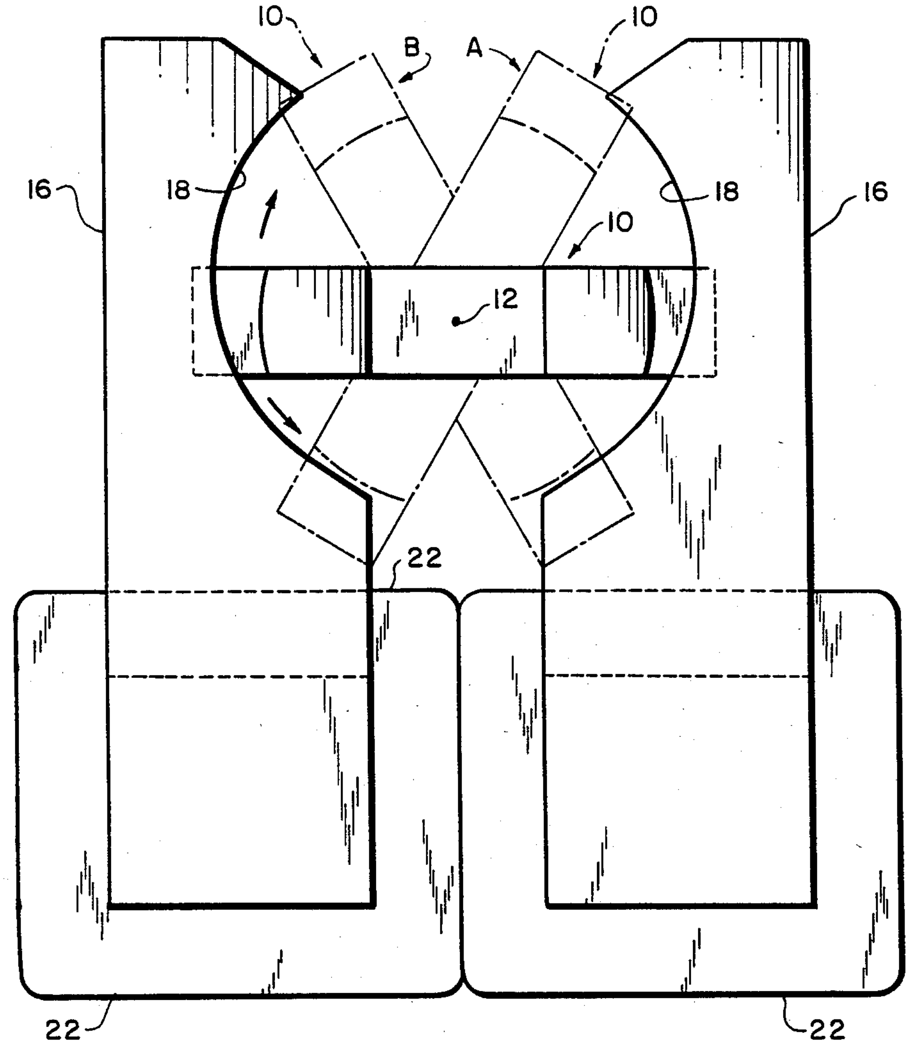
FIG. 3 is a side elevational view, partly schematic, of the ultrasonic scanning apparatus of FIG. 1 in the direction of arrow B.

A first embodiment of an ultrasonic scanning apparatus according to the invention is shown in FIGS. 1, 2 and 3. The apparatus includes a rotor 10 which is arranged to rotate about an axis of rotation 12 by using any suitable bearings (not shown). The rotor is made of a material having a positive magnetic susceptibility, such as a ferromagnetic material. The rotor 10 is preferably a ferrite or laminated iron, in order to reduce eddy current losses caused by passing a high frequency magnetic flux through the rotor. However, if small size is an important factor, rotor 10 is preferably solid iron. When solid iron is used, the frequency of the magnetic flux is made as low as possible within the constraints described further below.

The rotor 10 is provided with four pole faces 14. One pair of pole faces 14 is arranged on a first side of the axis of rotation 12, and the other pair of pole faces 14 is arranged on a second side of the axis of rotation 12, opposite the first side. All of the pole faces are oriented away from the axis of rotation 12.

The ultrasonic scanning apparatus also includes two electromagnetic stators 16. One electromagnetic stator 16 is arranged on a first side of the axis of rotation 12, and the other electromagnetic stator 16 is arranged on a second side of the axis of rotation 12, opposite the first side.

Each stator 16 has two curved pole faces 18 arranged opposite a pair of rotor pole faces 14. The stator pole faces 18 are separated from the associated rotor pole faces 14 by gaps.

Each of the stator pole faces 18 is tapered. Referring to FIG. 3, the stator pole faces 18 are tapered such that on counterclockwise rotation of the rotor 10, the gaps on the left side of the rotor decrease while the gaps on the right side of the rotor increase. Conversely, on rotation of the rotor 10 clockwise, the gaps on the right side of the rotor decrease and the gaps on the left side of the rotor increase.

Each electromagnetic stator 16 is made of a material having a positive magnetic susceptibility. Preferably, the electromagnetic stators are made of the same material as the rotor 10, for the same reasons discussed above.

Each electromagnetic stator 16 includes an electrically conductive coil 22 wrapped around a portion of the stator. By passing an electric current through the coil 22, magnetic flux lines are generated in the stator.

Each stator 16 and one-half of the rotor 10 form a magnetic circuit whose major reluctance is in the gaps. On energization of one coil 22, for example the left coil 22 in FIG. 3, magnetic flux is generated in the left side magnetic circuit. Due to the fact that such a circuit will tend to minimize its magnetic reluctance, the rotor 10 will rotate counterclockwise (to reduce the size of the gap) to position A.

By cutting power to the left coil 22, and by energizing the right coil 22, the rotor 10 can be made to rotate clockwise to position B.

Figure 4:
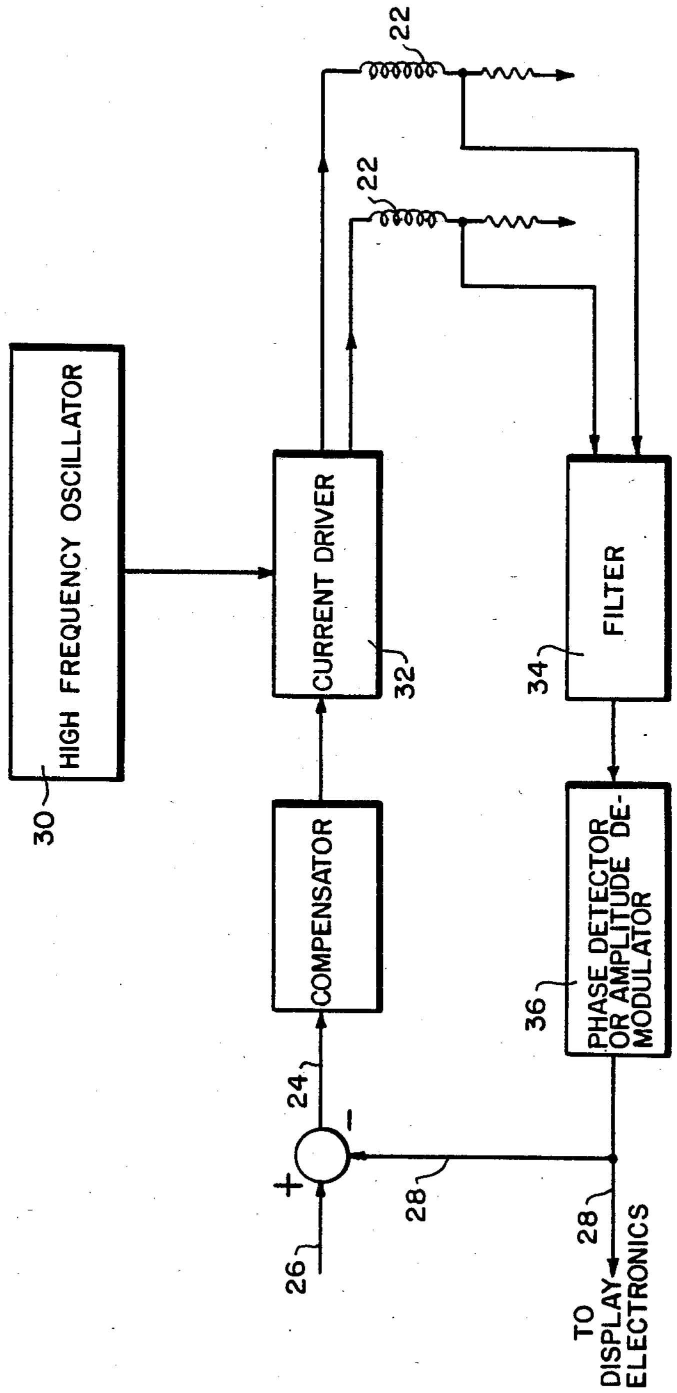
FIG. 4 is a block diagram of the feedback system according to the invention for controlling the angular position of the ultrasonic transducer as a function of time.

The coils 22 may be energized by using a control network as shown in FIG. 4. In this control system, the coils 22 are energized by a difference signal (or drive signal) 24 which represents the difference between the reference signal 26 and an angular position signal 28. The reference signal 26 represents the desired angular position of the rotor 10 as a function of time, and the angular position signal 28 represents the actual angular position of the rotor 10 around the axis of rotation 12.

As can be seen in FIG. 4, the difference signal 24 is compensated (for stability) and amplified in order to power the coils 22.

The angular position signal 28 is generated by first generating a high frequency signal in oscillator 30. The high frequency signal is then coupled into current driver 32 which thereby couples the high frequency signal into the coils 22. The high frequency signal is superimposed on the drive current of coils 22.

The angular position of the rotor 10 at any instant in time is uniquely related to the size of the gap between the rotor 10 and the stator 16. The size of the gap, in turn, will affect the reluctance of each magnetic circuit, which will affect the inductance of each coil 22. As a result, the high frequency voltage and current across each coil 22 will be a function of the angular position of the rotor 10.

The high frequency component of the coil current is separated from the low frequency drive signal 26 by the filter 34. A phase detector or amplitude demodulator 36 operates on the high frequency current component to produce a signal representing the angular position of the rotor 10. The angular position signal is made to be a linear function of the actual angular position of rotor 10 by empirically determining a suitable taper for each stator 16.

To avoid nonlinearities due to saturation of the rotor and stator with magnetic flux, it is advantageous to sense the angular position of the rotor by passing the high frequency signal through the coil 22 which, at any given instant, is not receiving the drive current. This can be accomplished with conventional switching circuits.

If the desired taper of stator 16 results in a signal which is a nonlinear function of angular position, this nonlinear function can be measured and stored in a read only memory device as a "look up table." Using conventional electronics, a linear angular position signal can be generated by comparing the demodulated high frequency signal to the "look up table."

Preferably, the reference signal component of the coil current and the drive signal 24 have a frequency of approximately 15 hertz. Preferably, the high frequency signal has a frequency of 1,000 hertz when a solid iron rotor is used (in order to keep eddy currents down to an acceptable level). The high frequency signal should be as high as possible above the drive signal to optimize the effectiveness of filter 34. When the rotor 10 is a ferrite or laminated iron, the high frequency signal can be 100,000 hertz because eddy currents will be smaller in these materials.

As shown in FIG. 4, a portion of the angular position signal 28 is subtracted from the reference signal 26. In addition, a portion of the angular position signal 28 is diverted to display electronics (not shown). The display electronics must "known" the angular position of the ultrasonic transducer 20 in order to correctly reconstruct, from the transducer's output signals, an image of the cross-sectional layer of the object being studied.

Figure 5:
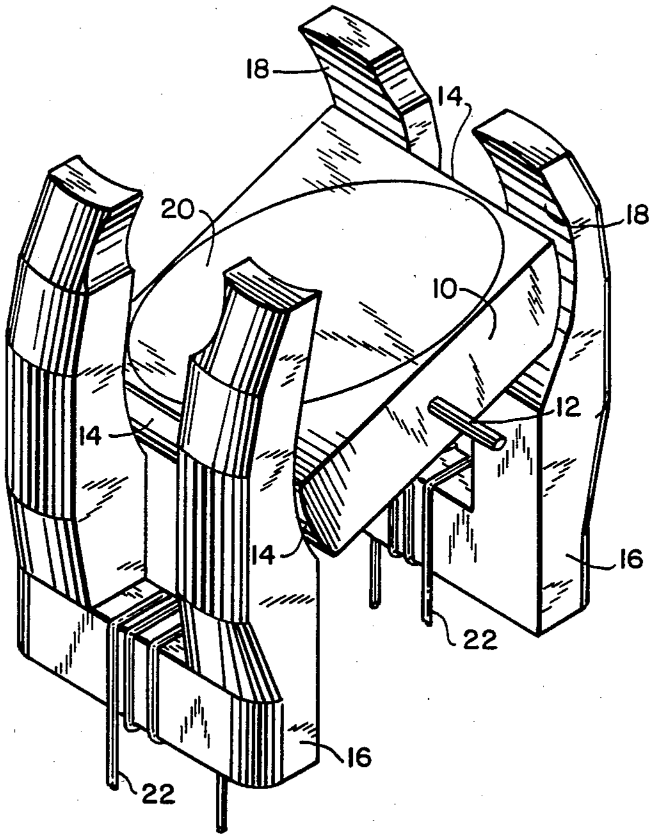
FIG. 5 is a perspective view of a second embodiment of an ultrasonic scanning apparatus according to the invention.

FIG. 5 shows a second embodiment of an ultrasonic scanning apparatus according to the invention. As in the above-described embodiment, the apparatus includes a rotor 10 having an axis of rotation 12. The rotor 10 has pole faces 14.

The scanning apparatus also includes two stators 16 having pole faces 18 and coils 22. As shown in FIG. 5, the stators 16 are tapered to vary the lengths of the gaps between the stator 16 and the rotor 10 as the rotor is turned on axis 12. Stators 16 are also tapered to vary the gap width as rotor 10 is rotated. The upper parts of stators 16 are narrowed to accomplish this latter function. By changing both gap length and width, the reluctance of each magnetic circuit can be made to change by a greater amount as rotor 10 rotates. This greater rate of change of reluctance increases the torque generated in the device.

What is claimed:

1. An ultrasonic scanning apparatus comprising:

a rotor having a positive magnetic susceptibility, said rotor being arranged to rotate about an axis of rotation, said rotor having first and second pole faces on a first side of the axis of the rotation, said first and second pole faces being spaced axially along the axis of rotation, said rotor having third and fourth pole faces on a second side of the axis of rotation opposite the first side, said third and fourth pole faces being spaced axially along the axis of rotation, said pole faces oriented away from the axis of the rotation;

a first electromagnetic stator means arranged on the first side of the axis of rotation, said first stator means having two curved pole faces arranged opposite the first and second rotor pole faces and separated therefrom by gaps, said first stator means pole faces being tapered such that on rotation of the rotor in a first direction from a first position to a second position, the gaps between the first stator means pole faces and the first and second rotor pole faces decrease, said first stator means and said rotor forming a first magnetic circuit whose major reluctance is in the gaps;

a second electromagnetic stator means arranged on the second side of the axis of rotation, said second stator means having two curved pole faces arranged opposite the third and fourth rotor pole faces and separated therefrom by gaps, said second stator means pole faces being tapered such that on rotation of the rotor in a second direction, opposite the first direction, from the second position to the first position, the gaps between the second stator means pole faces and the third and fourth rotor pole faces decrease, said second stator means and said rotor forming a second magnetic circuit whose major reluctance is in the gaps;

an ultrasonic transducer mounted on the rotor; and means for alternately energizing the first and second electromagnetic stator means to cause the rotor to oscillate about the axis of rotation.

2. An ultrasonic scanning apparatus as claimed in claim 1, characterized in that the energization means comprises:

means for generating an angular position signal representing the angular position of the rotor around the axis of rotation;

means for generating a reference drive signal representing the desired angular position of the rotor as a function of time; and control means for alternately energizing the first and second electromagnetic stator means in response to the difference between the angular position signal and the drive signal.

3. An ultrasonic scanning apparatus as claimed in claim 2, characterized in that the means for generating the angular position signal comprises means for measuring the reluctance of one magnetic circuit.

4. An ultrasonic scanning apparatus as claimed in claim 3, characterized in that the means for measuring the magnetic reluctance comprises:

means for generating a high frequency electric signal and coupling it into one of the electromagnetic stator means; and means for measuring changes in the high frequency signal due to its coupling to the electromagnetic stator means.

5. An ultrasonic scanning apparatus as claimed in claim 4, characterized in that each electromagnetic stator means comprises:

an element having a positive magnetic susceptibility; and an electrically conductive coil wrapped around the element.

6. An ultrasonic scanning apparatus as claimed in claim 5, characterized in that the stator means pole faces are tapered to vary the length of the gaps between the stator means pole faces and the rotor pole faces as the rotor is rotated; and on rotation of the rotor in the first direction, the lengths of the gaps between the first stator means pole faces and the first and second rotor pole faces decrease, and the lengths of the gaps between the second stator means pole faces and the third and fourth rotor pole faces increase.

7. An ultrasonic scanning apparatus as claimed in claim 6, characterized in that the stator means pole faces are tapered to vary the gap width as the rotor is rotated, and on rotation of the rotor in the first direction, the widths of the gaps between the first stator means pole faces and the first and second rotor pole faces increase, and the widths of the gaps between the second stator means pole faces and the third and fourth rotor pole faces decrease.

* * * * *